(12) United States Patent
Yamori et al.

(10) Patent No.: US 7,163,961 B1
(45) Date of Patent: Jan. 16, 2007

(54) DRUGS, FOODS AND ORAL COMPOSITIONS CONTAINING STILBENE-TYPE COMPOUNDS

(75) Inventors: Yukio Yamori, Kyoto (JP); Katsumi Ikeda, Kyoto (JP); Kenichi Mizutani, Kyoto (JP); Yasuhiro Kawai, Otsu (JP)

(73) Assignee: Sunstar Inc., Osaka (JP)

( * ) Notice: Subject to any disclaimer, the term of this patent is extended or adjusted under 35 U.S.C. 154(b) by 0 days.

(21) Appl. No.: 09/890,416

(22) PCT Filed: Jan. 28, 2000

(86) PCT No.: PCT/JP00/00454

§ 371 (c)(1),
(2), (4) Date: Jul. 27, 2001

(87) PCT Pub. No.: WO00/44370

PCT Pub. Date: Aug. 3, 2000

(30) Foreign Application Priority Data

Jan. 29, 1999 (JP) .................................. 11-022882
Mar. 12, 1999 (JP) .................................. 11-065797

(51) Int. Cl.
*A61K 31/05* (2006.01)
*A61K 36/87* (2006.01)
*C07C 39/12* (2006.01)

(52) U.S. Cl. ..................... 514/733; 424/766; 568/729
(58) Field of Classification Search ................ 424/766; 568/729; 514/733; 569/729
See application file for complete search history.

(56) References Cited

U.S. PATENT DOCUMENTS 6,048,903 A * 4/2000 Toppo et al.

FOREIGN PATENT DOCUMENTS

| CA | WO 00/38620 A2 * | 7/2000 |
| IT | WO 00/64282 A1 * | 11/2000 |
| WO | WO 99/01148 | 1/1999 |
| WO | WO 99/35917 A1 * | 7/1999 |
| WO | WO 99/56737 | 11/1999 |

OTHER PUBLICATIONS

Ruf et al, Arterioclerosis, Thrombosis and Vascular Biology, Platelet Rebound Effect of Alcohol Withdrawal and Wine Drinking in Rats. Relation to Tannins and Lipid Peroxidation, 1995, 156(1), pp. 140-144.*
Shepherd et al (The Lancet, Pravastatin in Elderly Individuals at Risk of Vscular Disease (PROSPER): A Randomised controlled Trial, 2002, 360, pp. 1623-1630.*
Shepherd et al (The New England Journal of Medicine, Prevention of Coronary Heart Disease With Pravastatin in Men With Hypercholesterolemia, 1995, 333(20), pp. 1301-1307.*
G. Calabrese Drugs Under Experimental and Clinical Research, vol. 25, No. 2/3, 1999, "Nonalcoholic Compounds of Wine: The Phytoestrogen Resveratrol and Moderate Red Wine Consumption During Menopause", pp. 111-114.
Jiangang Zou, et al. International Journal of Oncology, vol. 15, No. 4, "Suppression of Mitogenesis and Regulation of Cell Cycle Traverse by Resveratrol in Cultured Smooth Muscle Cells", pp. 647-651, 1999.
Kenichi Mizutani, et al., Biochemical and Biophysical Research Communications, vol. 253, No. 3, "Resveratrol Stimulates the Proliferation and Differentiation of Osteoblastic MC3T3-E1 Cells", pp. 859-863, 1998.
Leila Belguendouz, et al., Biochemical Pharmacology, vol. 55, No. 6, Interaction of Transresveratrol With Plasma Lipoproteins, pp. 811-816, 1998.
George J. Soleas, et al, Clinical Biochimisty, vol. 30, No. 2, "Resveratrol: A Molecule Whose Time Has Come? And Gone?", pp. 91-113, 1997.
David M. Goldberg, et al., American Chemical Society, Ser., vol. 661 (wine) "Identification and Assay of Trihydroxystilbenes in Wine and Their Biological Properties", pp. 24-43, 1997.
Chemical Abstracts, vol. 128, Abstract No. 317095, Columbus, Ohio, 1998, Krisa, S. et al./ Bull. Soc. Pharm. Bordeaux, vol. 136, No. 1-2-3-4, "Production, Isolation and Biological Activity of Piceids (stilbenes) Extracted From *Vitis vinifera* Cell Cultures", p. 7-18, 1997.

(Continued)

*Primary Examiner*—Paul A. Zucker
(74) *Attorney, Agent, or Firm*—Knobbe Martens Olson & Bear LLP

(57) ABSTRACT

The present invention provides a composition for preventing or treating diseases accompanied by a decrease in bone weight, hypertension and diseases resulting from hypertension, the composition containing, as an active component, at least one member selected from the a compound represented by formula (I)

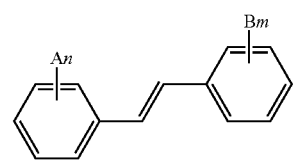

(1)

wherein A and B are the same or different and are independently selected from the group consisting of halogen, amino, amidino, anilinoamide, mercapto, sulfonic acid, phosphate, carboxy, hydroxy $C_1$–$C_5$ alkyl, sugar residue, —$OR^1$, and —$OCOR^2$; wherein $R^1$ is selected from the group consisting of hydrogen, $C_1$–$C_5$ alkyl, hydroxy $C_1$–$C_5$ alkyl, and $C_2$–$C_5$ alkenyl; and $R^2$ is selected from the group consisting of $C_1$–$C_5$ alkyl, hydroxy $C_1$–$C_5$ alkyl, and $C_2$–$C_5$ alkenyl; n is number of substituents A present and is a number from 0 to 5; and m is number of substituents B present and is a number from 0 to 5.

13 Claims, 2 Drawing Sheets

OTHER PUBLICATIONS

Chemical Abstracts, vol. 129, Abstract No. 310626, Columbus, Ohio 1998, Dadi Jin, et al., vol. 14, No. 2, "Polydatin protects against endotoxin shock in rats" pp. e20-e24, 1998.

Chemical Abstracts, vol. 76, Abstract No. 121647, Columbus, Ohio 1998, J. D. Geratz, et al, Arch. Int. Pharmacodyn. Ther. vol. 194, No. 2, "inhibition of the amidase and kininogenase activities of pancreatic kallikrein by aromatic diamidines and an evaluation of diamidines for their in vivo use", pp. 359-370, 1972.

Zhong-Fang Lai, et al., Japanese Journal of Pharmacology, vol. 72, No. 2, "Effects of Stibene Derivatives SITS and DIDS on Development of Intracellular Acidosis During Ischemia in Isolated Guinea Pig Ventricular Papillary Muscle in Vitro", pp. 161-174, 1996.

Ted Wilson, et al., Life Sciences, vol. 59, No. 1, "Resveratrol Promotes Atherosclerosis in Hypercholesterolemic Rabbits", PL15-PL21, 1996.

Yoshihiko Inamori, et al., Yakugaku Zasshi, vol. 104, No. 7, "The Coronary Vasodilatory and Hypotensive Effects of 3,3', 4,5'-Tetrahydroxystilbene and Its Derivatives", pp. 819-821, 1984, Chemical Abstracts, vol. 101, Abstract No. 163227, 1995.

G. Xu, et al., Yaoxue Xuebao, vol. 29, No. 11, "Inhibitition of Protein Kinase c by Stilbenoids", pp. 818-822, 1994 Chemical Abstracts, vol. 123, Abstract No. 78156, 1995.

Database WPI/CN/1127070 A/ Jul. 24, 1996.

Kenichi Mizutani, et al., *Biochem and Biophys. Research Communications*, vol. 253, No. 3, "Resveratrol Stimulates the Proliferation and Differentiation of Osteoblastic MC3T3-E1 Cells" 859-863 (1998).

Announcement Madis Botanicals, Inc., ResveraPure™ Resveratrol PE 8%, 1-2 (1997).

David M. Goldberg, et al., "Beyond Alcohol: Beverage Consumption and Cardiovascular Mortality," *Clinica Chimica Acta* 237 (1995) 155-187.

Cora Ke Chen, et al., "Vasorelaxing Activity of Resveratrol and Quercetin in Isolated Rat Aorta" *Gene. Pharmac.*, vol. 27, No. 2, pp. 363-366 (1996).

A.A.E. Bertelli, "Modulatory Effect of Resveratrol, a Natural Phytoalexin, on Endothelial Adhesion Molecules and Intracellular Signal Transduction," *Pharmaceutical Biology*, 1998, vol. 36, Supp. pp. 44-52.

Truelsen Thomas, et al., Database Biosis 'On Line! Biosciences Information Service' Intake of beer, wine and spirits and risk of stroke: The Copenhagen City Heart Study, Dec. 1998.

Messner Torbjorn, et al., Database Bios 'On Line! Biosciences Information Service' "Alcohol consumption and ischemic heart disease mortality in Sweden", 1996.

Food Composition and Nutrition Tables, 1989/90, p. 958.

I.O. Godfroid, *La Presse Medicale*, "Ĺéloge du vin?" Dec. 20, 1997, 26, No. 40, pp. 1971-1974 (No translation available).

Ezawa, Ikuko. "Basic and Practical Studies on Ca Metabolism and Privention [sic] of Osteoporosis." *J. Jpn. Soc. Nutr. Food Sci.* 49(5):245-257 (1996).

\* cited by examiner

DRUGS, FOODS AND ORAL COMPOSITIONS CONTAINING STILBENE-TYPE COMPOUNDS

This is the U.S. national phase under 35 U.S.C. § 371 of International application PCT/JP00/00454, filed Jan. 28, 2000, which claims priority to Japanese Patent Application No. 1999-22882, filed Jan. 29, 1999 and Japanese Patent Application No. 1999-65797, filed Mar. 12, 1999.

TECHNICAL FIELD

The present invention relates to various compositions containing a stilbene-type compound, more specifically, compositions which are useful in preventing or treating diseases accompanied by a decrease in bone weight and hypertension or diseases resulting from hypertension.

BACKGROUND ART

A bone tissue consists of osteocytes and an intercellular matrix, among which the latter is greater by weight. The intercellular matrix includes collagen fibers and inorganic constituents. This bone tissue undergoes constant remodeling to alter its form and to maintain the concentration of calcium in the blood. Usually, the bone weight of an adult hardly changes by the remodeling since the amounts of bone resorption and bone formation are equal. However, the condition that the amount of bone formation is less than to that of bone resorption causes osteopathy accompanied by a decrease in bone weight, including osteoporosis. The decrease in bone weight can be categorized into the following 3 groups by the factors considering the conditions of the bone remodeling: (1) decrease in bone weight associated with increased bone resorption function including osteoporosis in the early postmenopausal stage, hyperthyroidism or other diseases; (2) decrease in bone weight associated with a decrease in bone resorption and bone formation functions including senile osteoporosis, diabetic osteoporosis or the like; (3) decrease in bone weight resulting from an amount of bone resorption greater than the amount of bone formation despite of normal bone resorption and bone formation functions (for example, because of low calcium intake).

Thus, the crisis rate of osteoporosis increases for older people and dramatically rises in postmenopausal women.

Today, typical methods for treating or preventing osteopathy accompanied by a decrease in bone weight include (1) supplementing calcium/magnesium intake; (2) administration of calcitonin; (3) employing exercise therapy (particularly for aged people); (4) administration of active vitamin D (particularly for aged people); (5) administration of estrogen preparations (particularly for postmenopausal women) and (6) administration of parathyroid hormone; among others. These methods are usually carried out in combination, depending on the causes.

However, among the above methods, hormone preparation can not be used in prevention and has a high risk of side effects when used in treatment. Therefore, hormone preparation has to be used under a doctor's strict supervision. Further, other methods which do not use the hormone treatment in combination have not succeeded in producing satisfactory results. Accordingly, the development of side-effect-free treatments or prevention methods has been desired and many suggestions have been made on it. Typical research includes focusing on minerals having high absorption rates and combinations of these minerals (Japanese Unexamined Patent Publications No. 1987-501843 and No. 1994-500552), the suggestion focusing on the combined use of minerals and a substance which increases absorption rates of minerals (Japanese Unexamined Patent Publications No. 1994-40922 and No. 1994-70726), the suggestion focusing on the substance which improves the function of osteocytes (Japanese Examined Patent Publication No. 1995-76235 and Japanese Unexamined Patent Publication No. 1990-303457), among others.

However, the above suggestions can not satisfactorily prevent or treat osteopathy accompanied by a decrease in bone weight and the development of more effective methods is anticipated.

The periodontium, which supports the teeth and absorbs external force applied to the teeth, consists of the gingiva, the periodontal membrane, the alveolar bone and cementum. Advanced atrophy of gingival tissues and disease accompanied by the resorption of alveolar bone may result in permanent tooth loss. This greatly inconveniences a person's daily life, and is known to seriously affect a person's overall health by causing diseases such as nutrition disorders due to indigestion and the like. Although various treatments have been tested to prevent the resorption of important alveolar bone in the periodontium, improved prevention and treatment of atrophy of gingival tissues and the resorption of alveolar bone is desired.

Incidentally, among the three diseases having high death rate in Japan, cerebrovascular diseases and heart diseases are said to be closely associated with hypertensive diseases. Essential hypertension, which accounts for about 80% of all cases of hypertension, is associated with autonomic nerve and humoral factors including catecholamine and angiotensin in a complicated manner. In addition, it is known that the incidence rate of hypertension different between the sexes, that is, the incidence rate is higher among men than women. It is also confirmed that the incidence rate of hypertension increases among women over 50 years of age in their climacteric because of menopause. Women over 60 years of age have the same incidence rate of hypertension as men in the same age range.

Currently, hypertension can not be completely cured even by the administration of antihypertensive agents (medicines). Recent advances in food chemistry have led to the discovery of biologically active substances which are derived from various foods. Since these antihypertensive agents derived from foods are highly safe and economical, they are considered particularly useful in preventing or treating hypertension and diseases resulting from hypertension for long-term administration.

Incidentally, an experiment using cultured osteoblastic cell strain has recently revealed that a stilbene-type compound, resveratrol, accelerates the proliferation of osteoblastic cells, accelerates the activity of alkaline phosphatase and enhances the activity of prolyl hydroxylase (Biochemical and Biophysical Research Communications, Vol. 253, No. 3, pages 859–863, Dec. 30, 1998).

However, this report is simply an in vitro experiment using osteoblastic cells and it does not clearly indicate that the stilbene-type compound containing resveratrol is effective in treating or preventing diseases accompanied by a decrease in bone weight in complicated living organisms. In particular, it is unknown if stilbene-type compounds including resveratrol are effective treatment for diseases accompanied by a decrease in bone weight during and after climacteric or useful for treating or preventing hypertension and diseases resulting from hypertension.

DISCLOSURE OF INVENTION

An object of the present invention is to provide various compositions (pharmaceutical, food or oral compositions) which are effective in preventing or treating diseases accompanied by a decrease in bone weight, hypertension or diseases resulting from hypertension.

The inventors of the present invention conducted extensive research on biologically active substances found in plant components containing resveratrol. Consequently, the inventors found that the stilbene-type compound contained in large amounts in the plants of the Polygonaceae family, plants of the Vitaceae family, white hellebore (Veratrum album) and the like has a preventive or therapeutic effect on diseases accompanied by a decrease in bone weight; hypertension and diseases resulting from hypertension.

Moreover, the inventors also found that the combined use of the stilbene-type compound and at least one member selected from the group consisting of calcium, magnesium, vitamin C, vitamin D and vitamin K can synergistically produce excellent preventive and therapeutic effects on diseases accompanied by a decrease in bone weight.

The present invention was accomplished based on the above findings.

The present invention provides the following inventions.

First, the present invention provides a composition for preventing or treating diseases accompanied by a decrease in bone weight, the composition containing, as an active component, at least one member selected from a compound represented by formula (1)

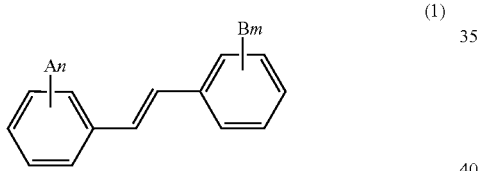

(1)

[wherein A and B are the same or different and each represents a halogen atom, an amino group, an amidino group, an anilinoamide group, a mercapto group, a sulfonic acid group, a phosphate group, a carboxy group, a hydroxy $C_1$ to $C_5$ alkyl group, a sugar residue, —$OR^1$ ($R^1$ represents a hydrogen atom, a $C_1$ to $C_5$ alkyl group, a hydroxy $C_1$ to $C_5$ alkyl group or a $C_2$ to $C_5$ alkenyl group.) or —$OCOR^2$ ($R^2$ represents a $C_1$ to $C_5$ alkyl group, a hydroxy $C_1$ to $C_5$ alkyl group or a $C_2$ to $C_5$ alkenyl group.).

n and m are the same or different and each is an integer from 0 to 5. There are n A's and m B's each of which may be the same or different.] and their multimers.

More specifically, the present invention provides the above composition which is a pharmaceutical composition or a food composition.

Further, the present invention provides the above composition, wherein the disease accompanied by a decrease in bone weight is any of climacteric diseases and post-climacteric diseases.

More specifically, the present invention provides the above composition, wherein the disease accompanied by a decrease in bone weight is osteoporosis, and the above composition, wherein the disease accompanied by a decrease in bone weight is that accompanied by resorption of alveolar bone (reduction of bone mass).

Particularly, when the diseases in the present invention are those accompanied by resorption of alveolar bone, the above compositions may be oral compositions.

More specifically, the present invention provides the above composition in which the compound represented by formula (1) and its multimers are derived from one or more plants selected from the group consisting of the plants of the Polygonaceae family, plants of the Vitaceae family, white hellebore (Veratrum album), mulberry and peanut.

In addition, the present invention provides the above composition in which the compound represented by formula (1) has substituents at at least positions 3, 5 and 4', the substituents being the same or different and any of a hydroxyl group, a sugar residue and —$OCOR^2$ [$R^2$ is as defined in the above.].

The present invention further provides the above composition containing one or more members selected from the group consisting of vitamin C, vitamin D, vitamin K, related compounds thereof; calcium and magnesium.

Furthermore, the present invention provides a method for preventing or treating diseases accompanied by a decrease in bone weight by taking or administrating an effective amount of at least one member selected from the above compounds represented by formula (1) and their multimers.

Secondly, the present invention provides a preventive or therapeutic composition for hypertension and diseases resulting from hypertension, the composition containing, as an active component, at least one member selected from the compounds represented by formula (1)

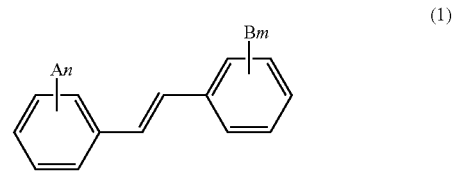

(1)

[wherein A and B are the same or different, and each represents a halogen atom, an amino group, an amidino group, an anilinoamide group, a mercapto group, a sulfonic acid group, a phosphate group, a carboxy group, a hydroxy $C_1$ to $C_5$ alkyl group, a sugar residue, —$OR^1$ ($R^1$ represents a hydrogen atom, a $C_1$ to $C_5$ alkyl group, a hydroxy $C_1$ to $C_5$ alkyl group or $C_2$ to $C_5$ alkenyl group.) or —$OCOR^2$ ($R^2$ represents a $C_1$ to $C_5$ alkyl group, a hydroxy $C_1$ to $C_5$ alkyl group, a $C_2$ to $C_5$ alkenyl group.).

n and m are the same or different and each is an integer from 0 to 5. There are n A's and m B's each of which may be the same or different.] and their multimers.

More specifically, the present invention provides the above composition which is a pharmaceutical composition or a food composition.

Moreover, the present invention provides the above composition in which the hypertension and diseases resulting from hypertension are climacteric and post-climacteric diseases.

Moreover, the present invention provides the above composition in which the hypertension and diseases resulting from hypertension are hypertension, arteriosclerosis, ischemic heart disease or cerebral apoplexy.

The present invention provides the above composition in which the compound represented by formula (1) and its multimers are derived from one or more plants selected from the group consisting of the plants of the Polygonaceae family, plants of the Vitaceae family, white hellebore (*Veratrum album*), mulberry and peanut.

Moreover, the present invention provides the above composition in which the compound represented by formula (1) has substituents at at least positions 3, 5 and 4', the substituents being the same or different and any of a hydroxyl group, a sugar residue and —OCOR$^2$ [R$^2$ is as defined in the above.].

Moreover, the present invention provides a method for preventing or treating hypertension and diseases resulting from hypertension by taking or administrating an effective amount of at least one member selected from the above compounds represented by formula (1) and their multimers.

BEST MODE FOR CARRYING OUT THE INVENTION

Figure 1:
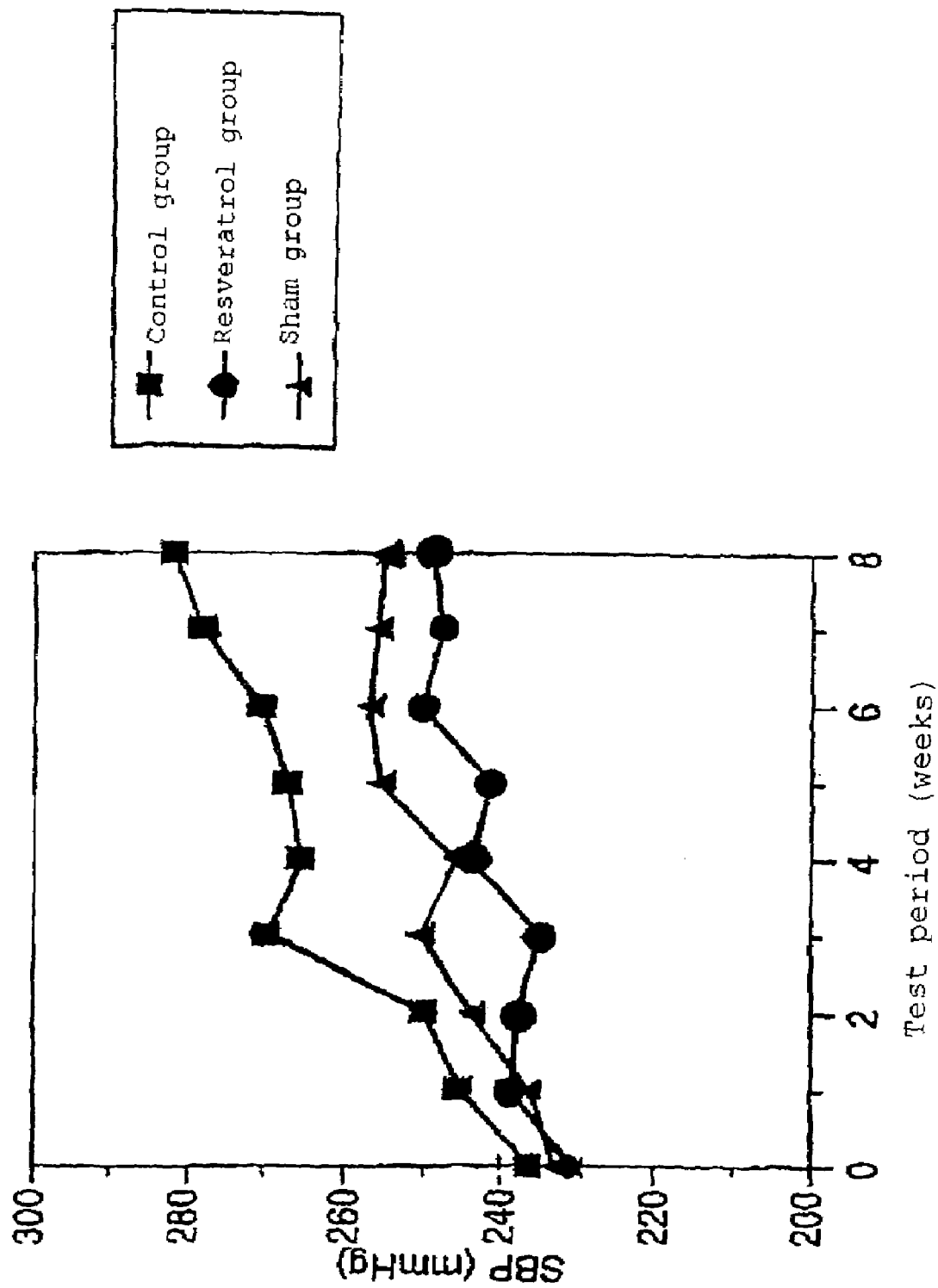
FIG. 1 shows resveratrol inhibiting a rise in blood pressure under climacteric conditions.

The composition of the present invention containing at least one of the compounds represented by formula (1) and its multimers (these will also be referred to as "stilbene-type compounds" in the present invention.) can be applied to prevent, treat, or alleviate diseases accompanied by a decrease in bone weights for example, osteoporosis and resorption of alveolar bone.

Further, the above stilbene-type compounds can be applied to prevent or treat hypertension and diseases resulting from hypertension since stilbene-type compounds have the action to lower blood pressure. In addition, a composition containing at least one member selected from the group consisting of the compounds represented by formula (1) and their multimers is also applicable to diseases which can be prevented or treated by lowering blood pressure. Therefore, the composition can also provide, for example, a pharmaceutical or food composition for preventing or treating arteriosclerosis by lowering blood pressure; a medical or food composition for preventing or treating ischemic heart disease by lowering blood pressure; and a pharmaceutical or food composition for preventing or treating cerebral apoplexy by lowering blood pressure.

The composition of the invention can be applied to the above diseases which occur during and after the climacteric. In the present invention, "climacteric" means a transitionary phase from a woman's reproductive period to senescence, more specifically, a few years before and after menopause (around the ages of 40 to 55). "post-climacteric" means the senescence after the climacteric. Therefore, in the present invention, "climacteric or post-climacteric" covers the period from the end of a woman's reproductive period to senescence, specifically, over the age of about 40. In the present invention, cases of climacteric conditions in pre-climacteric or premenopausal women who underwent an ovariectomy or have ovary dysfunction are included in "climacteric or post-climacteric".

In formula (1) of the invention, the groups are as follows.

Examples of the halogen atom include fluorine, chlorine, bromine, iodine and the like.

Examples of the C$_1$ to C$_5$ alkyl group include methyl, ethyl, n-propyl, isopropyl, n-butyl, sec-butyl, tert-butyl, n-pentyl and like straight-chain or branched alkyl groups.

Examples of the hydroxy C$_1$ to C$_5$ alkyl group include hydroxymethyl, hydroxy ethyl, hydroxy n-propyl, hydroxy isopropyl, hydroxy n-butyl, hydroxy n-pentyl and like straight-chain or branched hydroxyalkyl groups.

Examples of the C$_2$ to C$_5$ alkenyl group include vinyl, isopropenyl, allyl, 2-butenyl, 3-butenyl, 1-methylallyl, 2-pentenyl, 3-pentenyl and like straight-chain or branched alkenyl groups.

Examples of the sugar residue include those of pentose, hexose and like monosaccharides and their derivatives (e.g., deoxysugar, amino sugar, uronic acid, sugar alcohol, etc.); disaccharides; and trisaccharides and the like. In the present specification, "sugar residue" is a group whose hydrogen atom of the hydroxyl group bonded to the glycoside carbon atom at the reducing terminal of the sugar is removed.

Examples of the pentose include D-arabinose, L-arabinose, D-xylose, L-xylose, D-ribose, D-ribulose and the like.

Examples of the hexose include D-galactose, L-galactose, D-glucose, D-fructose, D-mannose, D-talose, L-sorbose, D-tagatose and the like.

Examples of the deoxysugar include the deoxysugar of the above-mentioned monosaccharides; and D-2-deoxyribose, L-rhamnose, L-fucose and the like.

Examples of the amino sugar include the amino sugar of the above-mentioned monosaccharides; and N-acetylglucosamine, N-acetylgalactosamine, N-acetylneuramic acid and the like.

Examples of the uronic acid include glucuronic acid, mannuronic acid, galacturonic acid, iduronic acid and the like.

Examples of the sugar alcohol include D-glucitol, D-mannitol, ribitol, galactitol and the like.

Examples of the disaccharide include the disaccharides obtained by suitably combining the above-mentioned monosaccharides, such as sucrose, lactose, trehalose, maltose, cellobiose, xylobiose, melibiose, rutinose, vicianose, trehalosamine, chondrosine and the like.

Examples of the trisaccharides include the trisaccharides obtained by suitably combining the above-mentioned monosaccharides, such as raffinose, maltotriose, cellotriose, manninotriose and the like.

In formula (1), n and m are each an integer from 0 to 5 and may be the same or different. Further, n A's and m B's may be the same or different.

The composition of the invention may contain a dimer, a trimer or like multimers, preferably dimer, trimer or tetramer of the compounds represented by formula (1). Examples of a trimer include α-viniferin; the trimer of resveratrol); examples of a dimer include ε-viniferin; the dimer of resveratrol); examples of a tetramer include hopeaphenol; the tetramer of resveratrol) and the like.

Shown below are the groups of preferable compounds among the compounds represented by formula (1) and their multimers.

(I) The compound in which both n and m are 0 [i.e., stilbene].

(II) The stilbene-type compounds in which n and m are the same or different and each is an integer from 0 to 5, and n A's and m B's are all hydroxyl groups (however, n and m are not 0 simultaneously.)

Specific examples include 4,4'-stilbenediol, 3,5-stilbenediol, resveratrol [i.e., 3,5,4'-stilbenetriol] and the like.

(III) The stilbene-type compounds in which n and m are the same or different and each is an integer from 0 to 5, and one of n A's and m B's is a sugar residue (however, n and m are not 0 simultaneously.)

Specific examples include rhaponticin (i.e., 4'-methoxy-3,3',5-stilbenetriol-3-glucoside), polydatin (i.e., piceid or 3,5,4'-stilbenetriol-5-glucoside), 3,4',5-stilbenetriol-4'-glucoside, 2,3,5,4'-stilbenetetraol-2-glucoside and the like.

(IV) The stilbene-type compounds in which n and m are the same or different and each is an integer from 0 to 5, and three substituents among the n A's and the m B's are bonded to positions 3, 5 and 4' (however, the sum of n and m are 3 or more.)

Specific examples include resveratrol, rhaponticin, polydatin, 3,4',5-stilbenetriol-4'-glucoside, 2,3,5,4'-stilbenetetraol-2-glucoside and the like.

(V) The stilbene-type compound in which n and m are the same or different and each is an integer from 1 to 5, and two substituents among the n A's and the m B's are bonded to positions 4 and 4'.

Specific examples include stilbamidine (i.e., 4,4'-diamidinostilbene), 4,4'-diaminostilbene, 4,4'-stilbenediol and the like.

(VI) The stilbene-type compounds in which n and m are the same or different and each is an integer from 0 to 5, at least one of the n A's and the m B's is a sulfonic acid group or carboxy group (however, both n and m are not 0 simultaneously.)

Specific examples include 4,4'-diamino-2,2'-stilbenedisulfonic acid, 2-carboxy-3,4'-stilbenediol and the like.

(VII) The stilbene-type compound in which n and m are the some or different and each is an integer from 0 to 5, and at least one of the n A's and the m B's is an alkoxy group (however, n and m are not 0 simultaneously.)

Specific examples include 4-methoxystilbene, 2,5'-dimethoxy-4,4'-stilbenediol and the like.

(VIII) The stilbene-type compound in which the n A's and the m B's are all —OR$^1$ (however, n and m are not 0 simultaneously.).

(IX) The dimers or trimers of the above compounds (I) to (VIII).

Specific examples include α-viniferin which is the trimer of resveratrol.

Among the above groups of the compounds, the stilbene-type compounds (II), (III) and (IV) are preferable. More preferable are the stilbene-type compounds in which has substituents at positions 3, 5 and 4', the substituents being the same$_2$ or different and each being a hydroxyl group, —OCOR$^2$ or a sugar residue, particularly preferable are resveratrol and polydatin. Further, preferable multimers are ε-viniferin and α-viniferin.

When the composition of the invention is a food composition, the stilbene-type compound is preferably a compound represented by formula (VIII).

The stilbene-type compound of the present invention can be synthesized in a conventional manner, for example, by Wittig reaction of a corresponding phosphonium salt with a corresponding aldehyde (cf. E. Reimann "Tetrahedron Letters" 47, 4051 (1970)).

The stilbene-type compounds of the present invention can be also prepared by drying, extracting or purifying plants containing the above compound, or by processing these plants by other methods. In the present invention, the resulting dried products, extracts and the like can be used as the compounds represented by formula (1) or their multimers. These dried products, extracts and the like used in the present invention are referred to as those "derived from plants".

For example, useful are plants which contain stilbene-type compounds of the invention in an amount of about 0.0001% by weight or higher when dried. Examples of such plants include the plants of the Polygonaceae family, the plants of the Vitaceae family, white hellebore (*Veratrum album*), mulberry, peanut and the like.

In the present invention, the useful plants of the Polygonaceae family are not particularly limited insofar as they contain the stilbene-type compound of the invention, Chinese indigo plant (*Polygonum tinctorium*), snakeweed (*Polygonum bistorta*), buckwheat (*Fagopyrum esculentum*), rhubarb (*Rheum* sp.), Chinese knotweed (*Polygonum multiflorum*), Japanese knotweed (*Polygonum cuspidatum*) and the like. Among these, particularly preferable are rhubarb (*Rheum* sp.), Chinese knotweed (*Polygonum multiflorum*), Japanese knotweed (*Polygonum cuspidatum*) because of the large amounts of the stilbene-type compounds contained therein. Chinese knotweed (*Polygonum multiflorum*) and Japanese knotweed (*Polygonum cuspidatum*) are more preferable since they contain large amounts of stilbene-type compounds.

The part of the plant used is not particularly limited, but rhizomes or roots are preferable.

The kinds of plants of the Vitaceae family used in the invention are not particularly limited insofar as they contain the stilbene-type compound of the invention.

A typical variety of the Vitaceae family is *Vitis* sp. More specifically, this variety includes the European and Middle Eastern varieties of *V.vinifera*, 15 North American muscadin varieties including *V.labrusca* and *V.California*, 2 North American muscadin varieties including *V.Munsoniana*, 3 Asian varieties including *V.Amurensis*, the varieties developed in Japan and the like. Among these, *V.vinifera*, *V.labrusca* and the varieties developed in Japan are preferable.

Specific examples of *V.vinifera* include Airen, Aligote, Riesling, Sauvignon blanc, Trebbiano, Chardonnay, Chenin blanc, Semillon, Muscat, Cabernet Sauvignon, Carignan, Cinsaut, Grenache Noir, Merlot, Mataro, Pinot Noir, Sangiovese, Syrah, Gamay, Grenache, Nebbiolo, Tempranillo, Gewurtraminer, Zweigltrebe, Muller-Thurgau, Grolleau, Cabernet Franc, Petit Verdot and the like.

Examples of *V.labrusca* include Zinfandel and the like.

Examples of the varieties developed in Japan include Koshu, Muscat Berry A, Black Queen and the like.

Among these, particularly preferable are Cabernet Sauvignon, Carignan, Merlot, Pinot Noir, Sangiovese, Syrah, Gamay, Grenache and Nebbiolo of the *V.vinifera* variety; the *V.labrusca* variety; Muscat Berry A and Black Queen because they contain large amounts of stilbene-type compounds.

The parts of these plants which are usable are not particularly limited, but leaves and fruits (including peels and seeds) are preferable. When using the fruits, unripe fruits are preferable since they contain a higher amount of stilbene-type compounds.

When using white hellebore (*Veratrum album*) (Liliaceae family), the parts which are usable are not particularly limited, but rhizomes are preferable.

When using mulberry, the parts which are usable are not particularly limited, but "mulberry fruits" are preferable.

The peanut (*Leguminosae Arachis*) used in the present invention is a plant of the Leguminoseae family. The parts of the peanut which are usable are not particularly limited, but preferable are "peas" or "pods" covering the same.

In the present invention, the aforementioned plants containing stilbene-type compounds may be subjected to natural drying, hot-air drying, freeze-drying or fermentation and then used as stilbene compounds represented by formula (1) or their multimers. Also usable are the concentrates, extracts, powders or the like prepared by processing the plants in a conventional manner. Extraction may be carried out by an extraction method using an organic solvent (including water), a method using supercritical extraction or like common extraction methods. Examples of such methods include that described in Japanese Unexamined Patent Publication No. 1986-171427 and the like.

The amount of stilbene-type compounds contained in the composition of the invention is not limited only insofar as the desired effects of the present invention can be achieved, and may be suitably selected depending on the form of the composition and other conditions. The amount of stilbene-type compound is preferably 0.0001% to 5% by weight, more preferably 0.001% to 1% by weight, particularly 0.005% to 1% by weight. These ranges are favorable in terms of solubility, palatability and the like.

The addition of one or more members selected from the group consisting of calcium and magnesium; vitamin C, vitamin D and vitamin K and related compounds thereof increases the effect of the composition of the invention in the prevention or treatment of diseases accompanied by a decrease in bone weight.

In the present specification, the related compounds of vitamin C, vitamin D and vitamin K are the precursors, derivatives and the like of these vitamins, including the compounds which have actions similar to those of these vitamins in the body.

As calcium, the composition of the invention may contain calcium lactate, calcium citrate, calcium gluconate and like organic calcium; calcium carbonate, calcium phosphate and like inorganic calcium, among others.

In the composition of the invention, it is preferable to use calcium derived from milk, animal bones and like animal materials; calcium derived from oyster shells, sea urchin shells, corals and like marine products; or calcium derived from dolomite ores and like lime components.

The calcium content in the composition of the invention is such that the daily amount taken or administered of calcium is preferably 100 to 1000 mg, more preferably 400 to 600 mg. The above ranges are favorable since they involve no risk of contracting circulatory system diseases due to an overdose of calcium even when administered or taken for a long period.

As magnesium the composition of the invention may contain magnesium lactate, magnesium citrate, magnesium gluconate and like organic magnesium; magnesium carbonate, magnesium phosphate and like inorganic magnesium.

In the composition of the invention, it is preferable to use magnesium obtained from magnesium lactate, magnesium gluconate, magnesium sulfate, magnesium chloride, bittern, coral, dolomite ore and the like. Among them, more preferably used is the magnesium obtained from magnesium lactate, magnesium gluconate, coral, dolomite ore and the like.

The amount of magnesium is not particularly limited insofar as the desired effects of the present invention can be achieved and may be suitable determined. Under normal circumstances, the daily dose of magnesium is preferably 50 to 2000 mg, more preferably 250 to 500 mg.

In the composition of the invention, it is preferable to use magnesium and calcium in combination. The ratio of calcium to magnesium when used in combination is, calculated based on the weight of the elements, preferably between 1:2 and 2:1, more preferably between 1:1 and 2:1.

Examples of vitamin C and related compounds include ascorbic acid, monodehydroascorbic acid, dehydroascorbic acid, erythorbic acid, D-erythroascorbic acid and the salts thereof (e.g., calcium salts, magnesium salts), ascorbic acid-2-phosphate, ascorbic acid-2-glucoside and like vitamin C derivatives.

The amount of the vitamin C and related compounds used is not particularly limited insofar as the desired effects of the present invention can be achieved and may be suitably selected. The amount is preferably such that the daily dose of vitamin C is 50 to 1000 mg, particularly preferably such that the daily dose is 500 to 1000 mg. Excessive intake of vitamin C may cause diarrhea, but the above-specified range does not involve such a risk.

Examples of the vitamin D and related compounds include ergosterol, 7-dehydrocholesterol, 22-dihydroergosterol, 7-dehydrositosterol, 7-dehydro-stigmasterol, 7-dehydrocampesterol, ergocalciferol, cholecalciferol, vitamin $D_4$, vitamin $D_5$, vitamin $D_6$, vitamin $D_7$, their derivatives and the like. Among these, ergocalciferol, cholecalciferol and their derivatives are preferable.

The amount of the vitamin D and related compounds is not particularly limited insofar as the desired effects of the present invention can be achieved and may be suitably selected. Preferably, the amount of the vitamin D and related compounds is such that the daily dose of the compound is 50 to 800 IU (International Unit), more preferably such that the daily dose of the vitamin D and related compounds is 100 to 400 IU. Excessive intake of vitamin D for a long period may cause a D-hypervitaminosis, but the above-specified range does not involve such a risk.

Examples of the vitamin K and related compounds include phylloquinone; menaquinone; 2-methyl-1,4-naphthoquinone and like 2-methylnaphthoquinone derivatives and the like. Among these, phylloquinone and menaquinone are particularly preferable.

The amount of the vitamin K and related compounds used is not particularly limited insofar as the desired effects of the present invention can be achieved and may be suitably selected. Preferably, the daily dose of vitamin K is 0.04 to 30 mg, more preferably the daily dose of vitamin K is 0.08 to 1 mg.

Particularly in case that the composition of the invention is a pharmaceutical composition to treat or prevent diseases accompanied by resorption of alveolar bone, the therapeutic effects can be further increased by using one or more bone dysbolism therapeutic agents in combination, if necessary. Examples of bone dysbolism therapeutic agents include retinol, retinoic acid and like vitamin A compounds; cholecalciferol, ergosterol, 7-dehydrocholesterol, 22-dihydroergosterol, 7-dehydrositosterol, 7-dehydrostigmasterol, 7-dehydrocampesterol, ergocalciferol, cholecalciferol, vitamin $D_4$, vitamin $D_5$, vitamin $D_6$, vitamin $D_7$ and like vitamin D compounds; phylloquinone, menaquinone, menadione and like vitamin K compounds; prostaglandin $E_1$, prostaglandin $E_2$ and like prostaglandin compounds; calcitonin; parathyroid hormone, adrenocortical hormone and like hormonal compounds having hormone-like actions; somatomedin, epidermal growth factor, nerve growth factor, cartilage derived factor, osteonectin, osteocalcin and like growth factors; cytokine; lymphokines; and diphosphonate compounds. The content of these agents in the composition is 0.00001 to 0.1% by weight, preferably about 0.0001 to 0.01% by weight.

When used medicinally, the composition of the invention can be prepared by conventional methods for prevention or treatment in the form of powders, granules, tablets, capsules, solutions, injections (solutions, suspensions), ointments, creams, gels, plasters and other forms. In addition, when the composition of the invention is used medicinally to treat or prevent diseases accompanied by resorption of alveolar bone, the composition of the invention can be used for injections, percutaneous administration drugs, oral drugs, per-oral-mucous administration drugs and injection preparations for the periodontal pocket by conventional methods.

The preferable amount of the compounds of formula (1) or their multimers (stilbene-type compounds) used in the composition of the invention is as mentioned above. The content in the preparation is preferably 0.0001% by weight or higher in the case of an injection, 0.05% by weight or higher in the case of percutaneous administration drug, and 0.005% by weight or higher in the case of an oral drug. Further, the content is preferably 0.005% by weight or higher in the case of a per-oral-mucous administration drug in a medicine for preventing or treating diseases accompanied by resorption of alveolar bone.

The method for administrating the compounds of formula (1) or their multimers (stilbene-type compounds) is not particularly limited, and depends on the form of the composition. For example, powders, granules, tablets, capsules and solutions can be administered orally; injections can be administered intravenously, intramuscularly, intradermally, subcutaneously or intraabdominally; and ointments, creams, gels, plasters and the like can be applied for percutaneous absorption. Among these administration methods, the composition of the invention is preferably administered percutaneously or orally. When the composition of the invention is administered as a medicine for treating or preventing diseases accompanied by resorption of alveolar bone, it is preferably absorbed through the oral mucosa or injected into the periodontium.

When the composition of the invention is used as an oral composition to treat or prevent diseases accompanied by resorption of alveolar bone, the composition may be added to liquids, pastes, ointments, powders and the like. These compositions can be used in the forms of dentifrices, liquid dentifrices, mouthwashes, mouth sprays, oral liniments and the like. An oral liniment can be applied to the oral cavity using floss, a swab and like materials or applicators. In this case, the preferable amount of stilbene-type compounds is as mentioned above. When used in an oral composition, the amount of stilbene-type compounds is preferably 0.005% by weight or higher.

When the composition of the invention is taken as a food, it can be prepared in various forms such as blocks, liquids, syrups, powders, jellies and the like, by conventional methods. Specific examples of such forms include soft drinks, juice, tea and like beverages (ampuled liquid medicines); powdered juice, powdered soup and like powdered beverages; cookies, biscuits, cereals, chewable tablets, chewing gums, candies, gummy candies, wafers, senbei (Japanese rice crackers) and like confections; dressing, sauce, powdered seasoning and like seasonings; bread, noodles, mochi (rice cake) and like staple food products; fish paste products; foods designed for sick people, foods for specified health uses, dietary supplement and like functional foods, among others. When the composition of the present invention is taken as a food composition for preventing diseases accompanied by resorption of alveolar bone, candies, chewing gums, gummy candies and chewable tablets are preferable preparations because they remain in the oral cavity for a long period when taken.

The food composition of the present invention can be also used as a foodstuffs (e.g., a food additive) to prepare any food. When used as a foodstuff, the food of the invention may be added to a food preparation, for example, commercially available beverages and the like. The preferable content of the stilbene-type compound in the food composition is as mentioned in the above, but more preferably 0.0005% by weight or higher.

The composition of the invention may be mixed with, as necessary, substances commonly used for medicines, foods and oral preparations unless the effects of the invention are lowered. Examples of such substances include other pharmaceutically effective substances, nutrients, animal and plant components, excipients, extenders, sweeteners, flavoring agents, coloring agents, preservatives, emulsifiers, solubilizing agents, hydrotropes and the like.

The composition of the invention may be mixed with the compound of formula (1) or its multimers and various known components depending on its form in its preparation, and may be in various forms and formulations such as pharmaceutical compositions, food compositions and oral compositions.

When taken as food, the composition of the invention is preferably taken together with proteins to mitigate the astringent taste characteristics of stilbene-type compounds. More preferably, the composition of the invention is mixed with milk or dairy products or milk protein is added to the composition.

The amount of the composition of the invention to be administered or taken may be suitably selected depending on the form of the composition; age, sex and other attributes of the patient or recipient, severity of the disease, and the like.

More specifically, the amount of stilbene-type compounds of the invention, when taken in daily diet for prevention for a long period, is about 0.1 to 500 mg, preferably about 0.5 to 100 mg, more preferably about 1 to 50 mg per adult per day.

When stilbene-type compounds are positively administered or taken orally for the purpose of mitigating symptoms or treatment, the amount of stilbene-type compounds is typically about 1 to 500 mg, preferably about 10 to 500 mg, more preferably about 10 to 100 mg per adult per day. When stilbene-type compounds are administered directly into the body by intravenous injection or by other methods, the amount of the stilbene-type compound is preferably about 0.01 to 50 mg per adult per day.

The composition of the invention may be administered or taken in a single dose or in several doses daily. The various compositions of the invention can be administered to or taken by humans and administered to or fed to animals. Particularly, when the composition of the invention is used to prevent or treat a decrease in bone weight, it is effectively used by climacteric and post-climacteric women.

INDUSTRIAL APPLICABILITY

Because the stilbene-type compound represented by formula (1) and its multimers have various actions including inhibiting a decrease in bone weight and lowering blood pressure, etc., pharmaceutical, food and oral compositions containing the compound and its multimers of the invention are useful for preventing or treating diseases accompanied by a decrease in bone weight, hypertension and diseases resulting from hypertension.

When the composition of the invention is used to prevent or treat a decrease in bone weight, it can be used for, e.g., women over 30.

Food composition of the invention having the aforementioned effects can be also taken as a functional food such as a foods designed for sick people, foods for specified health uses, dietary supplements and the like.

When the composition of the invention further contains one or more members selected from the group consisting of calcium, magnesium, vitamin C, vitamin D and vitamin K, the composition can be used especially to treat or prevent diseases accompanied by a decrease in bone weight very effectively.

EXAMPLES

Below, the present invention will be explained in further detail referring to the Examples and the Experimental Examples. However, the present invention is not limited to these Examples. The values of the amounts are "% by weight" or "part by weight" unless otherwise specified.

The resveratrol used in the following Examples is a product of Sigma Company Limited, "Trans-Resveratrol" (resveratrol content: 98% by weight or higher).

Experimental Example 1

Preventive Action on Diseases Accompanied by a Decrease in Bone Weight

Rats subjected to climacteric conditions were studied to estimate the effect of the composition of the invention in preventing a decrease in bone weight.

Specifically, 18-week-old female stroke-prone spontaneously hypertensive rats (SHRSP/izm) were ovariectomized and subjected to climacteric conditions. Then, the rats were grouped into a resveratrol group to which resveratrol was administered and a control group. Also provided was a sham group of rats which received a sham operation, that is, a laparotomy without ovary removal.

The rats were fed ad libitum. The control group and sham group were fed with "Powdery Mixed Feed SP" (manufactured by Funahashi Farm), and the resveratrol group was fed with the same feed with resveratrol added thereto. The amount of added resveratrol administered was adjusted to about 20 mg/kg per day. Each group had 5 rats that were bred for 8 weeks. After the breeding period, the rats were slaughtered for dissection. The left thigh bone was removed from each group's rats. The thigh bones were tested for their bone density and measured for their breaking load and breaking energy values using "EZ-test" (manufactured by Shimadzu Corporation), whereby their bone strength was evaluated. The results are shown in Table 1.

TABLE 1

| | Bone density (g/cm$^3$) | Breaking load (N) | Breaking energy (J) |
|---|---|---|---|
| Control Group | 1.447 ± 0.231 | 83.30 ± 17.16 | 0.0351 ± 0.0032 |
| Resveratrol Group | 1.479 ± 0.281 | 99.46 ± 9.57 | 0.0523 ± 0.0073 |
| Sham Group | 1.502 ± 0.356* | 95.53 ± 23.64 | 0.0487 ± 0.0141* |

Average values and standard deviations are shown in the table (n = 5).
*Significant difference from the control group was found ($p < 0.05$).

The results shown in Table 1 reveal that the resveratrol group had bone density, bone breaking load and bone breaking energy higher than the control group. Thus, it was confirmed that taking resveratrol helps prevent the diseases accompanied by a decrease in bone weight associated with climacteric.

Experimental Example 2

Preventive Action on Hypertension, Cardiac Hypertrophy and Cerebral Apoplexy Rats subjected to climacteric conditions were studied to estimate the effect of the composition of the invention in preventing a rise in blood pressure, cardiac hypertrophy and cerebral apoplexy.

Specifically, 18-week-old female stroke-prone spontaneously hypertensive rats (SHRSP/izm) were ovariectomized and subjected to climacteric conditions. Then, the rats were grouped into a resveratrol group and a control group. Also provided a sham group of rats which received a sham operation, that is, a laparotomy without ovary removal.

The rats were fed ad libitum. The control group and sham group were fed with "Powdery Mixed Feed SP" (manufactured by Funahashi Farm), and the resveratrol group was fed with the same mixed feed with 1.5 g/kg of resveratrol added. Five rats in each group were bred for 8 weeks. The blood pressure of the rats was measured every week without anesthesia by means of a rat caudal artery sphygmomanometer. After the breeding period, the rats were slaughtered for dissection. The ratio of the weight of the heart to the total body weight and the ratio of the weight of the brain to the total body weight of the rats were determined, and the brain tissue of the rats was observed for cerebral infarction and cerebral hemorrhage. The results are shown in FIG. 1 and Table 2.

TABLE 2

| | Heart weight per body weight (%) | Brain weight per body weight (%) |
|---|---|---|
| Control group | 0.527 ± 0.056 | 1.133 ± 0.194 |
| Resveratrol group | 0.424 ± 0.023 | 0.803 ± 0.02 |
| Sham group | 0.517 ± 0.035% | 1.065 ± 0.149% |

Average values and standard deviations are shown in the table (n = 5).

The resveratrol group indicated a significantly higher action to inhibit a rise in the blood pressure than the control group. The blood pressure of the resveratrol group was about the same as that of the sham group. In addition, the resveratrol group had significantly lower heart weight and brain weight than the control group. Further, cerebral infarction was found in 4 rats out of 5 in the control group but was not found in any rats in the resveratrol group. These results confirmed that resveratrol lowers blood pressure, inhibits cardiac hypertrophy and prevents the onset of cerebral apoplexy.

Experimental Example 3

Preventive Action on Hypertension and Cardiac Hypertrophy

The ability of the composition of the invention to prevent a rise in blood pressure and cardiac hypertrophy was researched using male rats.

Figure 2:
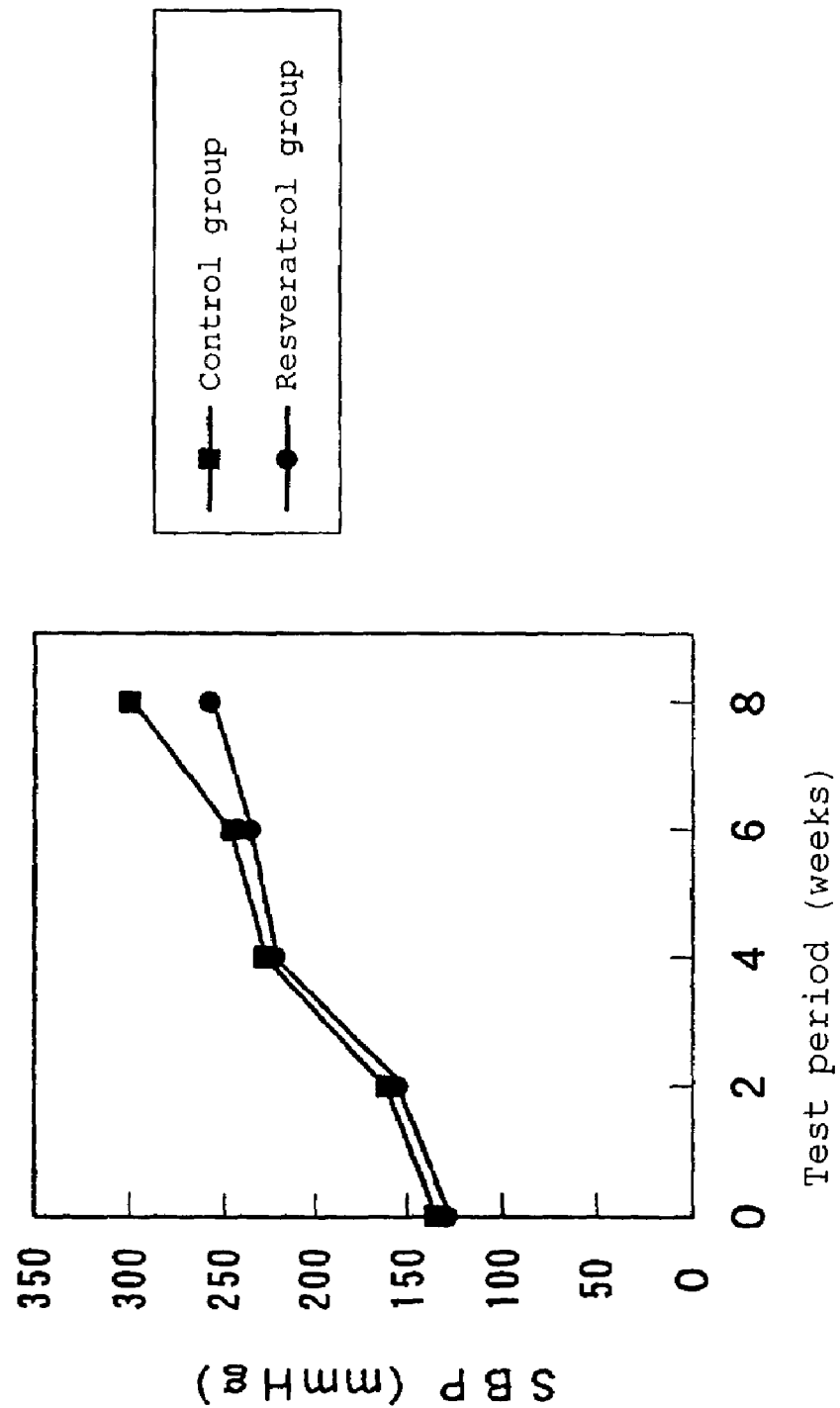
FIG. 2 shows how resveratrol inhibits a rise in blood pressure.

Firstly, 5- to 6-week-old male stroke-prone spontaneously hypertensive rats (SHRSP/izm) were grouped into a resveratrol group and a control group. The rats were fed ad libitum with "Powdery Mixed Feed SP" (manufacture by Funahashi Farm). The resveratrol group was administered resveratrol in an amount of 5 mg/kg per day. The administration was conducted by the intended clinical route, i.e., orally. The rats were force-fed orally once a day with a Teflon gastric tube. The dose was adjusted to 1 ml per 100 g of the body weight using a water for injection listed in The Japanese Pharmacopoeia, calculated according to the measured body weight of the individual rats. The control group was given the same amount of the water for injection listed in the Japanese Pharmacopoeia only. Each group had 5 rats that were bred for 8 weeks. The blood pressure of the rats was measured every 2 weeks without anesthesia by means of a rat caudal artery sphygmomanometer. After the breeding period, the rats were slaughtered for dissection and the ratio of the weight of the heart to the total body weight of the rats was measured. The results are shown in FIG. 2 and Table 3.

TABLE 3

|  | Heart weight per body weight (%) |
| --- | --- |
| Control group | 0.595 ± 0.024 |
| Resveratrol group | 0.557 ± 0.024 |

Average values and standard deviations are shown in the table (n = 5).

The resveratrol group indicated a significantly higher action to inhibit a rise in the blood pressure and lighter heart weight than the control group. Therefore, it was confirmed that resveratrol lowers blood pressure and inhibit cardiac hypertrophy.

Example 1

Sugar-Coated Tablet A sugar-coated tablet was prepared in a conventional manner by mixing the ingredients according to the following formula.

| Ingredient | Amount (part by weight) |
| --- | --- |
| Dolomite (calcium content: 20%, magnesium content: 10%) | 59.65 |
| Powdered reducing malt sugar syrup | 20 |
| Lactose | 15 |
| Sucrose fatty acid ester | 4 |
| Zinc-containing yeast (zinc content: 2600 ppm) | 1 |
| Crystalline cholecalciferol | 0.25 |
| Resveratrol | 0.1 |
|  | 100 |

The obtained sugar-coated tablet can be administered or taken, for example, for the purpose of remedying the symptoms of osteoporosis and preventing hypertension.

Example 2

Plaster for Percutaneous Administration

A plaster for percutaneous administration was prepared in a conventional manner by mixing the ingredients according to the following formula.

| Ingredient | Amount (part by weight) |
| --- | --- |
| Polyvinyl alcohol | 15 |
| Ethyl alcohol | 10 |
| Sodium carboxymethyl cellulose | 5 |
| Propylene glycol | 3 |
| Perfume | 0.5 |
| Resveratrol | 0.1 |
| Purified water | q.s. |
|  | 100 |

The obtained plaster can be used, for example, for remedying bone dysbolism.

Example 3

Tablet

A tablet was prepared in a conventional manner by mixing the ingredients according to the following formula.

| Ingredient | Amount (part by weight) |
| --- | --- |
| Palatinose | 52.145 |
| Collagen protein hydrolysate (Gelita sol D1, manufactured by DGF Stoess AG) | 30 |
| Calcium carbonate | 10 |
| Magnesium carbonate | 5 |
| Sucrose fatty acid ester (Ryoto SE S-370F, manufactured by Mitsubishi-Kagaku Foods Corporation) | 2 |
| Flavor | 0.5 |
| Crystalline cholecalciferol | 0.3 |
| Aspartame | 0.05 |
| Resveratrol | 0.005 |
|  | 100 |

The obtained tablet can be administered or taken to prevent or treat osteoporosis or hypertension.

Example 4

Beverage

A beverage was prepared by mixing ingredients by the following preparation method.

Into a 25% solution of skim milk powder was inoculated a starter, i.e., pre-cultured lactic acid bacteria (*Streptococcus lactis*), in a concentration of 1% by weight. The bacteria was cultured until the pH of the solution was about 4, producing yogurt. After the breeding peried, the yogurt was homogenized. A sweetening additive agent was prepared by dissolving 6.5 parts of sugar, 10 parts of orange juice and 30 parts of pectin in 60 parts of water, and was added to the homogenized yogurt to achieve a sweetening agent to yogurt ratio of 4:5 by weight. This mixture was then blended together. Further, 10 parts of a 2:1 (by weight) mixture of calcium gluconate and magnesium gluconate was dissolved in water to prepare a solution. An amount of the solution (equaling 20% of the total weight of final mixture) was added to the mixture of yogurt and sweetening agent. This mixture was then blended together. Finally, grape leaf extract (resveratrol content: 0.05%) was added to the mixture in a concentration of 10% by weight, based on the total amount of the final mixture containing the grape leaf extract, thereby creating the beverage.

The obtained beverage can be administered or taken, for example, for preventing or treating osteoporosis or for preventing the diseases accompanied by resorption of alveolar bone. The beverage is preferably administered to or taken by aged post-climacteric people.

Example 5

Plaster for Bone Dysbolism Remedy in the Oral Cavity

A plaster for bone dysbolism remedy in the oral cavity was prepared in a conventional manner by mixing the ingredients according to the following formula.

| Ingredient | Amount (part by weight) |
|---|---|
| Glycerin | 76.9 |
| Triacetin | 17.0 |
| Hydroxyethyl cellulose | 4.0 |
| Copolymer of ethyl acrylate, methyl methacrylate and methacryloyl ethyl trimethyl ammonium chloride | 2.0 |
| Resveratrol | 0.1 |
| | 100.0 |

Example 6

Food for Preventing Diseases Accompanied by Resorption of Alveolar Bone

A tablet for preventing diseases accompanied by resorption of alveolar bone was prepared in a conventional manner by mixing the ingredients according to the following formula.

| Ingredient | Amount (part by weight) |
|---|---|
| Collagen protein hydrolysate (Gelita sol D2, manufactured by DGF Stoess AG) | 30.0 |
| Calcium carbonate | 10.0 |
| Magnesium carbonate | 5.0 |
| Sucrose fatty acid ester (Ryoto SE S-370F, manufactured by Mitsubishi-Kagaku Foods Corporation) | 2.0 |
| Flavor | 0.5 |
| Crystalline cholecalciferol | 0.3 |
| Aspartame | 0.05 |
| Resveratrol | 0.005 |
| Palatinose | q.s. |
| | 100.0 |

Example 7

Dentifrice

A dentifrice was prepared in a conventional manner by mixing the ingredients according to the following formula.

| Ingredient | Amount (part by weight) |
|---|---|
| Calcium pyrophosphate | 42.0 |
| Glycerin | 20.0 |
| Grape peel extract (containing 0.005% by weight of resveratrol) | 10.0 |
| Sucrose fatty acid ester (Ryoto SE S-370F, manufactured by Mitsubishi-Kagaku Foods Corporation) | 2.0 |
| Sodium lauryl sulfate | 1.5 |
| Carrageenan | 1.0 |
| Flavor | 1.0 |
| Sodium lauroyl sarcosinate | 0.5 |
| Stevia extract (Rebaudio A9-50GR, manufactured by Morita Kagaku Kogyo Co., Ltd.) | 0.1 |
| Purified water | q.s. |
| | 100.0 |

Example 8

Mouthwash

A mouthwash was prepared in a conventional manner by mixing the ingredients according to the following formula.

| Ingredient | Amount (part by weight) |
|---|---|
| Ethyl alcohol | 40.0 |
| Glycerin | 15.0 |
| Grape marc extract (containing 0.001% by weight of resveratrol) | 10.0 |
| Sucrose fatty acid ester (Ryoto SE S-370F, manufactured by Mitsubishi-Kagaku Foods Corporation) | 2.0 |
| Polyoxyethylene (60) hydrogenated castor oil | 1.0 |
| Flavor | 0.5 |
| Stevia extract (Rebaudio A9-50GR, manufactured by Morita Kagaku Kogyo Co., Ltd.) | 0.01 |
| Chlorohexidine | 0.005 |
| Purified water | q.s. |
| | 100.0 |

What is claimed is:

1. A method for increasing bone breaking load and strength in a mammal comprising:
   identifying a mammal having a need for increased bone breaking load and strength; and
   administering to said mammal at least one member selected from the compound represented by Formula (1) or a multimer thereof from about 0.1 mg per day to about 20 mg per kg per day:

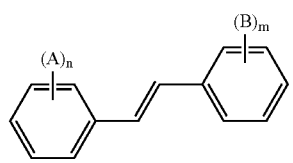

wherein A and B are the same or different and are independently selected from the group consisting of halogen, amino, amidino, anilinoamide, mercapto, sulfonic acid, phosphate, carboxy, hydroxy $C_1$–$C_5$ alkyl, sugar residue, —$OR^1$, and —$OCOR^2$;

wherein $R^1$ is selected from the group consisting of hydrogen, $C_1$–$C_5$ alkyl, hydroxy $C_1$–$C_5$ alkyl, and $C_2$–$C_5$ alkenyl; and $R^2$ is selected from the group consisting of $C_1$–$C_5$ alkyl, hydroxy $C_1$–$C_5$ alkyl, and $C_2$–$C_5$ alkenyl;

n is number of substituents A present and is a number from 0 to 5; and m is number of substituents B present and is a number from 0 to 5.

2. A method for preventing cerebral apoplexy in a mammal, comprising administering to said mammal a composition comprising an effective amount of at least one member selected from the compound represented by Formula (1) or a multimer thereof from about 0.1 mg per day to about 20 mg per kg per day:

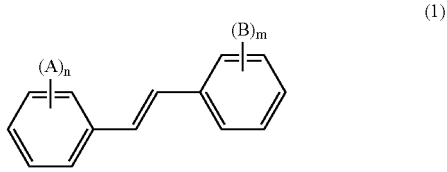

wherein A and B are the same or different and are independently selected from the group consisting of halogen, amino, amidino, anilinoamide, mercapto, sulfonic acid, phosphate, carboxy, hydroxy $C_1$–$C_5$ alkyl, sugar residue, —$OR^1$, and —$OCOR^2$;

wherein $R^1$ is selected from the group consisting of hydrogen, $C_1$–$C_5$ alkyl, hydroxy $C_1$–$C_5$ alkyl, and $C_2$–$C_5$ alkenyl; and $R^2$ is selected from the group consisting of $C_1$–$C_5$ alkyl, hydroxy $C_1$–$C_5$ alkyl, and $C_2$–$C_5$ alkenyl;

n is number of substituents A present and is a number from 0 to 5; and m is number of substituents B present and is a number from 0 to 5;

wherein said composition does not contain ethanol.

3. The method according to claim 1, wherein the mammal has a menopausal or postmenopausal disease.

4. The method according to claim 1, wherein said compound is part of a pharmaceutical formulation.

5. The method according to claim 1, wherein said compound is part of a food product.

6. The method according to claim 1, wherein the mammal has a disease accompanied by a decrease in bone weight that is accompanied by resorption of alveolar bone.

7. The method according to claim 6, wherein said compound is adapted for oral administration performed by a medium selected from the group consisting of dentifrice, liquid dentifrice, mouthwash, mouth spray, oral liniment, swab, and floss.

8. The method according to claim 1, wherein the compound represented by Formula (1) is obtained from at least one plant selected from the group consisting of plants of Polygonaceae family, plants of Vitaceae family, white hellebore (*Veratrum album*), mulberry, and peanut.

9. The method according to claim 2, wherein said compound is part of a pharmaceutical formulation.

10. The method according to claim 2, wherein said compound is part of a food product.

11. The method according to claim 2, wherein cerebral apoplexy is present in menopausal or post-menopausal period.

12. The method according to claim 2, wherein the compound represented by Formula (1) is obtained from at least one plant selected from the group consisting of plants of Polygonaceae family, plants of Vitaceae family, white hellebore (*Veratrum album*), mulberry, and peanut.

13. The method of claim 2, further comprising identifying a mammal at increased risk for cerebral apoplexy prior to administering said composition.

* * * * *